(12) United States Patent
Paik et al.

(10) Patent No.: US 9,970,911 B2
(45) Date of Patent: May 15, 2018

(54) GAS SENSOR PACKAGE

(71) Applicant: LG INNOTEK CO., LTD., Seoul (KR)

(72) Inventors: Jee Heum Paik, Seoul (KR); Ji Hun Hwang, Seoul (KR)

(73) Assignee: LG INNOTEK CO., LTD., Seoul (KR)

( * ) Notice: Subject to any disclaimer, the term of this patent is extended or adjusted under 35 U.S.C. 154(b) by 257 days.

(21) Appl. No.: 14/487,452

(22) Filed: Sep. 16, 2014

(65) Prior Publication Data

US 2015/0075257 A1    Mar. 19, 2015

(30) Foreign Application Priority Data

Sep. 16, 2013 (KR) .................. 10-2013-0111261
Mar. 25, 2014 (KR) .................. 10-2014-0034575

(51) Int. Cl.
*G01N 33/00* (2006.01)
*G01N 27/12* (2006.01)

(52) U.S. Cl.
CPC ..... *G01N 33/0027* (2013.01); *G01N 33/0009* (2013.01); *G01N 33/0042* (2013.01); *G01N 27/123* (2013.01)

(58) Field of Classification Search
CPC .... G01N 27/04; G01N 27/041; G01N 27/123; G01N 33/0004; G01N 33/0009; G01N 33/0027
USPC ..... 73/31.05, 31.06; 204/424, 425, 428, 431
See application file for complete search history.

(56) References Cited

U.S. PATENT DOCUMENTS

| | | | |
|---|---|---|---|
| 4,980,042 A | 12/1990 | Shiomi et al. | |
| 5,530,202 A * | 6/1996 | Dais ................ | H05K 9/0026 174/385 |
| 7,787,250 B2 * | 8/2010 | Li ..................... | H01L 23/04 361/715 |
| 2007/0107493 A1 * | 5/2007 | Katsuda .......... | G01N 33/0009 73/23.31 |
| 2008/0250847 A1 | 10/2008 | Kitani et al. | |
| 2009/0033344 A1 * | 2/2009 | Hiratsuka ........ | G01N 27/04 324/693 |
| 2010/0230297 A1 | 9/2010 | Wahl et al. | |
| 2010/0230766 A1 | 9/2010 | Elian et al. | |
| 2010/0244166 A1 * | 9/2010 | Shibuta .......... | H01L 27/14618 257/432 |
| 2011/0147803 A1 | 6/2011 | Henneck et al. | |
| 2015/0075258 A1 * | 3/2015 | Paik ................ | G01N 27/041 73/31.06 |

(Continued)

FOREIGN PATENT DOCUMENTS

CN    101359008    2/2009
CN    101853827    10/2010

(Continued)

OTHER PUBLICATIONS

European Search Report issued in Application EP 15 16 0793 dated Aug. 10, 2015.

(Continued)

*Primary Examiner* — Benjamin Schmitt
(74) *Attorney, Agent, or Firm* — Ked & Associates, LLP

(57) ABSTRACT

A gas sensor package includes a substrate, a gas sensing element on the substrate, and a cover module including ventilation holes.

13 Claims, 8 Drawing Sheets

(56) References Cited

U.S. PATENT DOCUMENTS

2015/0090002 A1* 4/2015 Paik ................ B81B 7/0061
73/31.06
2015/0198551 A1* 7/2015 Jun ................. H01L 23/3107
204/431

FOREIGN PATENT DOCUMENTS

| JP | 2002-195979 | 7/2002 |
| JP | 2012-098234 | 5/2012 |

OTHER PUBLICATIONS

Matthias Budde et al., "The TECO Envboard: a Mobile Sensor Platform for Accurate Urban Sensing—and More;" Networked Sensing Systems (INSS), 2012, Ninth International Conference on, IEEE, Jun. 11, 2012 pp. 1-2, XP032206949, DOI: 10.1109/INSS.2012.6240573; ISBN: 978-1-4673-1784-9.
Chinese Office Action issued in Application 201410471651.9 dated Dec. 27, 2017 (full Chinse text and full English translation).

\* cited by examiner

[Fig. 1]
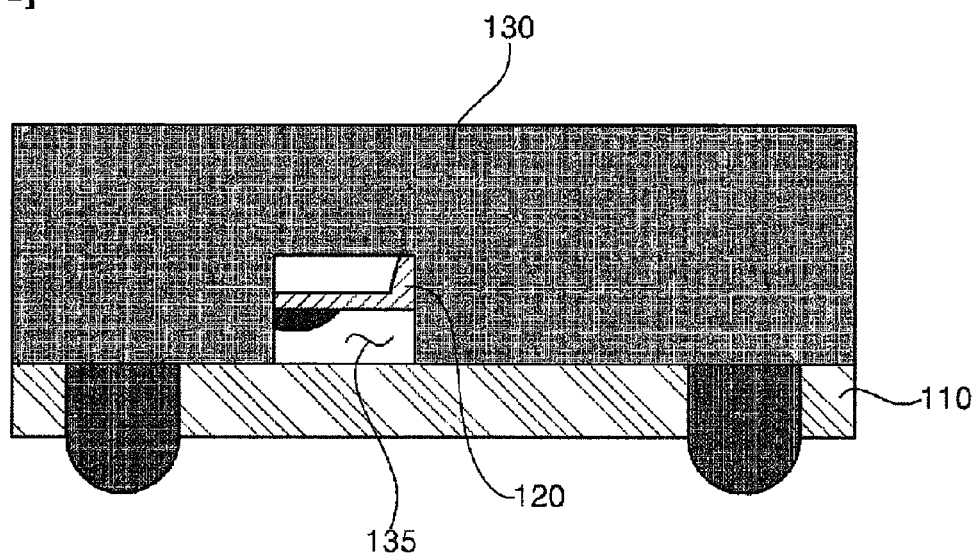
[Fig. 2]
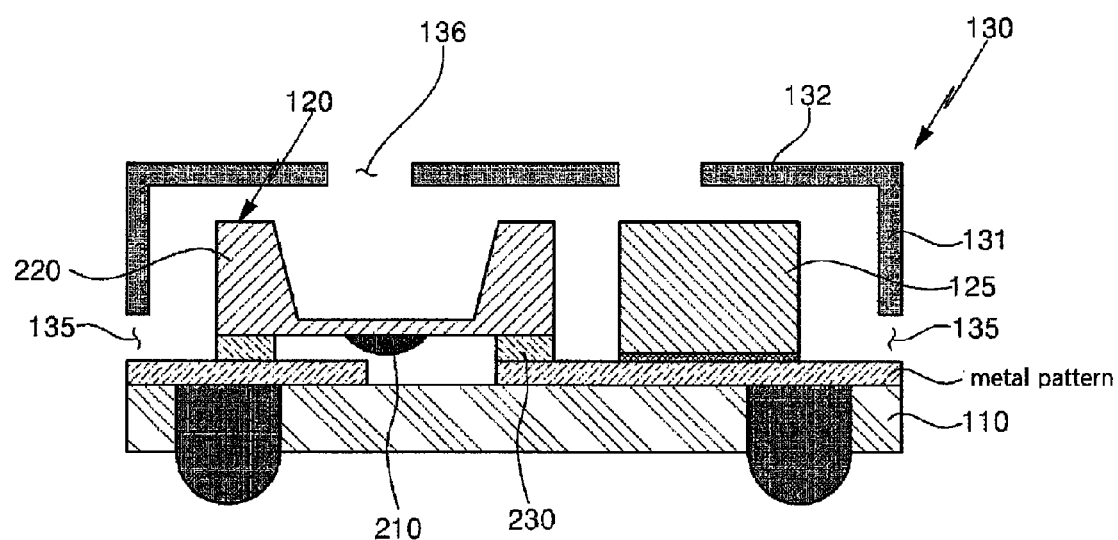

[Figure 10]
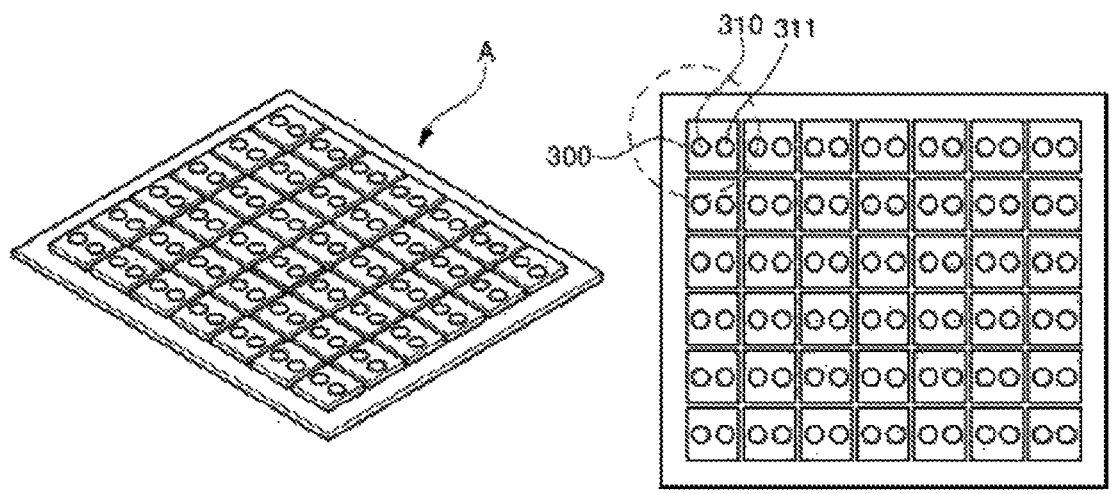
Figure 11
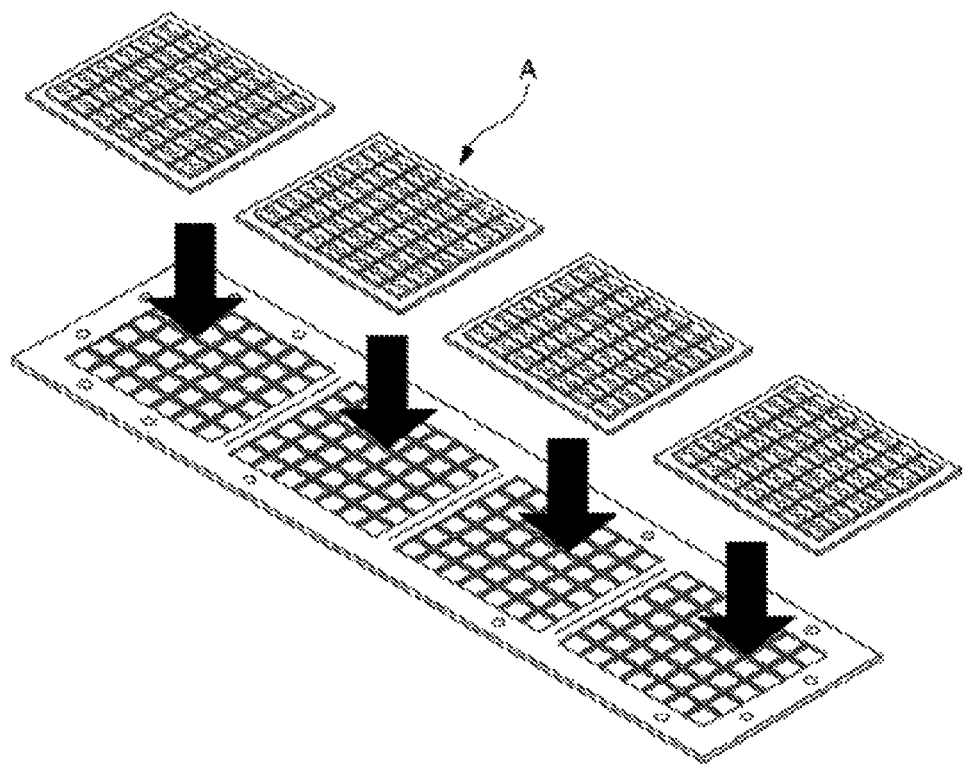

GAS SENSOR PACKAGE

CROSS-REFERENCE TO RELATED APPLICATIONS

This application claims priority to Korean Patent Application No. 10-2013-0111261, filed on Sep. 16, 2013, and No. 10-2014-0034575, filed on Mar. 25, 2014, in the Korean Intellectual Property Office, the entire contents of which are hereby incorporated by reference.

BACKGROUND

1. Field

The present disclosure relates to a gas sensor package.

2. Background

A gas sensor is needed to have characteristics, such as speed showing how fast the gas sensor can respond to a situation, sensibility which can respond to the detection of gas in spite of the detection of a small amount of the gas, durability showing how long the gas sensor can operate, economic efficiency showing that the sensor can be used by consumers without burdens, and the like.

In order for the gas sensor to be combined with an existing semiconductor process technology, the gas sensor should have characteristics of the easiness of integration and enumeration. A home gas leakage alarm made of tin oxide (SnO2) as a material has come into wide use as a practical gas sensor.

The gas sensor is divided into a semiconductor type using a change of resistance values according to a change in the amount of gas and an oscillator type using a change in an oscillation frequency generated when gas is absorbed onto an oscillator, which oscillates with a predetermined frequency. Most of the gas sensors have been used as the semiconductor type gas sensors having simple circuits and showing a stable thermal property at room temperature.

In general, a gas sensor has a package structure in which a gas sensing material or a sensing chip is mounted to the gas sensor, and should have a separate cap member for protecting an upper surface of the gas sensing material or the sensing chip, and a mesh-shaped member formed of minute nets is provided on an upper surface of the cap member so as to allow the ventilation of gas.

In this gas sensing package for sensing gas, a height of an upper structure is increased due to the cap member and the mesh-shaped member, and an entire size of the gas sensing package is further increased up to several times to dozens of times than that of a sensor chip because a wire bonding method is used when the sensor chip is connected to an electrode part. Due to this, there is a limit to implement miniaturization of the gas sensor.

BRIEF DESCRIPTION OF THE DRAWINGS

The embodiments will be described in detail with reference to the following drawings in which like reference numerals refer to like elements wherein:

The accompanying drawings are included to provide a further understanding of the present disclosure, and are incorporated in and constitute a part of this specification. The drawings illustrate exemplary embodiments of the present disclosure and, together with the description, serve to explain principles of the present disclosure. In the drawings:

FIGS. 1 to 3 are views for explaining a gas sensor package according to an embodiment of the present disclosure;

FIG. 10 is a view illustrating a cover module according to another embodiment of the present disclosure; and FIGS. 11 and 12 are views for explaining a method of manufacturing the gas sensor package according to the embodiment of the present disclosure.

DETAILED DESCRIPTION OF THE INVENTION

Figure 3:
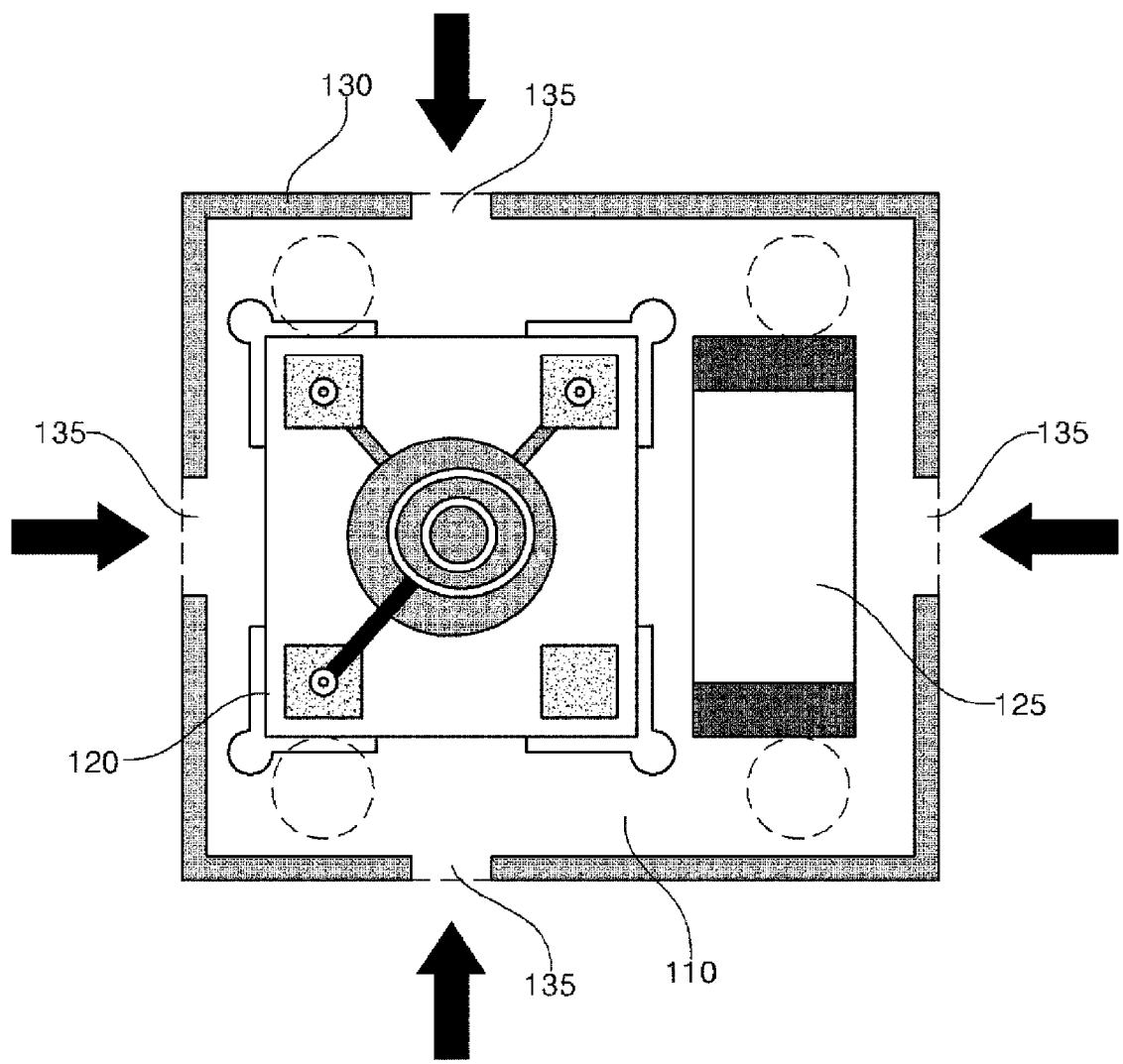

FIGS. 1 to 3 are views for explaining a gas sensor package according to an embodiment of the present disclosure. That is, FIG. 1 is a side view of the gas sensor package, FIG. 2 is a cross-sectional view of a side of the gas sensor package, and FIG. 3 is a cross-section view of an upper part of the gas sensor package.

A gas sensing element 120 is disposed at a substrate 110 to sense gas. The gas sensing element 120 may include a gas sensing portion 210 for detecting gas using a sensing material which enables gas sensing and gas sensing structures which have been commercialized, may be called the gas sensing element. A sensing element using an oxide semiconductor, a sensing element using a carbon nanotube, various other sensing semiconductor chips and the like may be applied as the gas sensing element.

As illustrated in FIGS. 2 and 3, the gas sensing element 120 may be mounted to the substrate 110 in a flip chip bonding method. An electrode pattern 230 of the gas sensing element 120 is directly bonded to a metal pattern of the substrate 110 in a flip chip bonding method so that a bonding wire can be removed, thereby enabling miniaturization of the gas sensor package and a reduction of production costs.

A cover module 130, which is an element intended for protecting the gas sensing element 120, may be configured for covering the gas sensing element 120 and may be made of a metal material. The cover module 130 may include ventilation holes 135, 136, and as illustrated in FIGS. 1 and 2, on the cover module 130, the first ventilation hole 135 is formed to contact the substrate 110, and the ventilation holes 135, 136 may be formed to communicate with a receiving space 137 of an inner portion of the cover module 130.

As illustrated in FIG. 2, the cover module 130 may include side wall portions in contact with the substrate 110, and an upper surface portion 132 on the side wall portions 131, and the first ventilation hole 135 may be formed on the side wall portions 131. The first ventilation hole 135 may be formed to contact the substrate 110.

The upper surface portion 132 of the cover module may be formed parallel to a plane of the substrate 110 and the side wall portions 131 of the cover module may be formed perpendicular to the plane of the substrate 110. When the ventilation holes 135, 136 are formed in the cover module 130, the ventilation holes may be formed by performing selectively etching using a photo lithography process.

The ventilation hole 135 enables a reaction gas to sufficiently flow into the gas sensing element 120, thereby ensuring the ventilation. As illustrated in FIG. 3, the first ventilation hole 135 is symmetrically formed based on the gas sensing element 120, thereby facilitating effective flow of the reaction gas. The first ventilation hole 135 may be configured such that at least one first ventilation hole 135 may be formed in each of the side wall portions 131, and as illustrated in FIG. 2, the first ventilation hole may be formed to contact the substrate 110.

As illustrated in FIG. 2, the second ventilation holes 136 may be configured such that the multiple second ventilation holes 136 are formed in the upper surface portion 132 of the cover module 130, and the second ventilation holes 136 may discharge the reaction gas entered into the cover module 130. The first ventilation hole 135 or the second ventilation holes 136 may be aligned to correspond to a center part of the gas sensing element 120.

With regard to a bonding wire method, due to a height of the bonding wire, a height of the cover module should be higher than that of the cover module used in the other methods should be used. With regard to a flip chip bonding method, a height of the cover module may be formed in a height of the element. Due to this, the problems of flow and discharge of the reaction gas are generated.

According to the embodiment of FIGS. 1 to 3, the reaction gas may sufficiently flow into the gas sensing element 120 in the cover module 130 via the first ventilation hole 135, and the reaction gas within the cover module 130 may be discharged via the second ventilation holes 136, thereby facilitating effective ventilation. The problems of ventilation and radiant heat may be simultaneously settled.

As illustrated in FIGS. 2 and 3, the gas sensor package may further include an output change part 125 as well as the gas sensing element 120 on the substrate 110, and the output change part 125 may be mounted on the substrate in a flip chip bonding method. The output change part 125 is electrically connected to the gas sensing element 120, thereby changing an output mode of the gas sensing element 120.

The output change part 125 may be composed of a passive element for changing the output of a resistance mode to the output of a voltage mode. A fixed resistance element or an NTC (negative temperature coefficient) thermistor electrically connected to metal patterns and the gas sensing element may be used as the passive element. The output change portion 125 may be applied to various IT devices (including smart phones) by packaging a resistance output mode of the gas sensing element 120 as a voltage output mode.

By connecting a fixed resistance element or an NTC (negative temperature coefficient) thermistor to a side of the gas sensing element 120, the resistance output mode may be converted into the voltage output mode. When the NTC (negative temperature coefficient) thermistor is connected to the side of the gas sensing element, a resistance change value is compensated for an initial sensing material according to each temperature, and thus it is advantageous in that a regular initial voltage value can be maintained.

When a resistance element or a NTC thermister is used in the outside of the PCB, it is problematic in that a size of an entire module is increased and separate circuit design should be performed. However, when the gas sensor package including the output change portion capable of converting an output mode into a voltage mode in an inner part thereof is implemented, the miniaturized gas sensor may be provide. Furthermore, when to a resistance change value of the NTC thermister for each temperature is adopted in the same rate as a resistance curve of the sensing material, the temperature can be compensated, so that initial resistance of the sensing material according to a change in temperature can be compensated.

The output change portion 125, which is configured as above, is formed on the substrate 110 as the gas sensing element 120, and the output change portion is also configured to be covered by the cover module 130.

Figure 4:
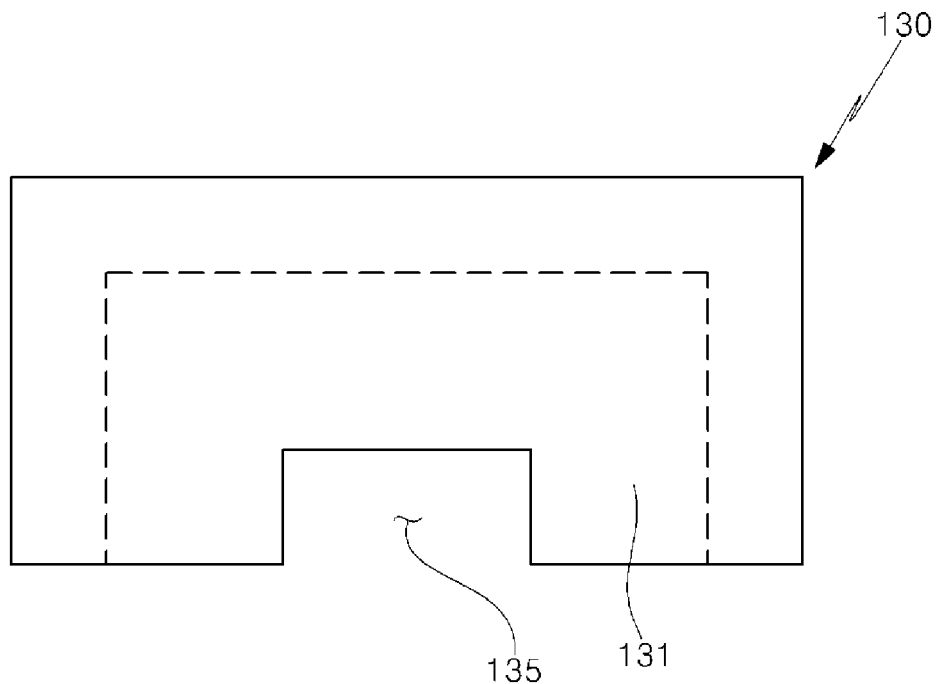
FIGS. 4 and 5 are views illustrating a cover module according to an embodiment of the present disclosure.
Figure 5:
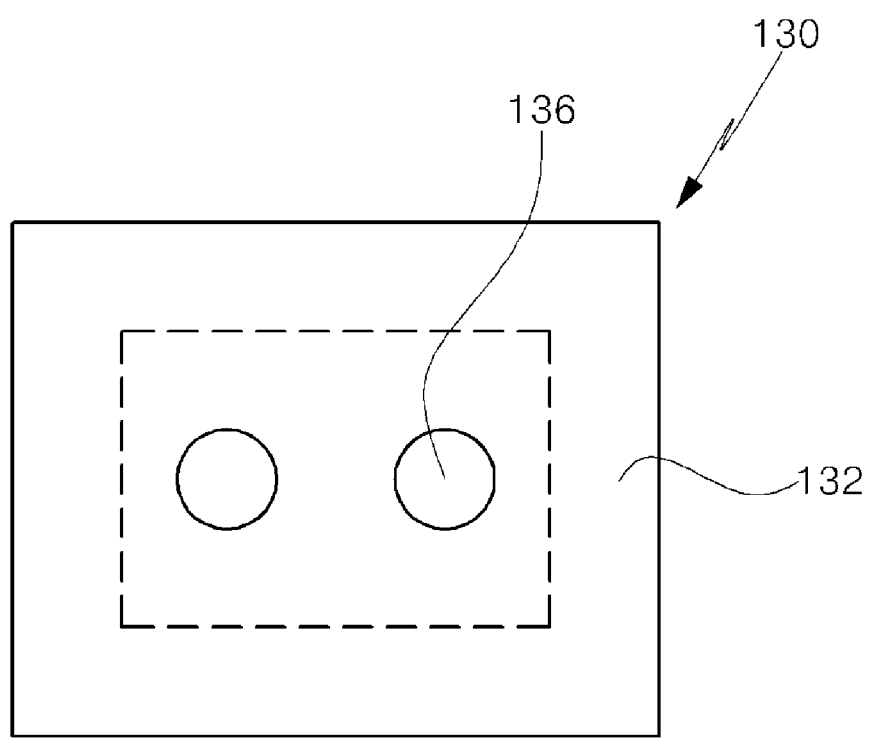

FIGS. 4 and 5 are views illustrating a cover module according to an embodiment of the present disclosure. FIG. 4 is a side view of the cover module, and FIG. 5 is a top view of the cover module according to the embodiment of the present disclosure. As illustrated in FIG. 4, the first ventilation hole 135 is formed at each of the side wall portion 131 of the cover module 130. As illustrated in FIG. 5, the second ventilation holes 136 is formed in the upper surface portion 132 of the cover module 130.

The first ventilation hole 135 may enable a reaction gas to sufficiently flow into the gas sensing element 120, thereby ensuring ventilation. The second ventilation holes 136 may be formed in the upper surface portion 132 of the cover module 130 so as to effectively discharge the reaction gas entered into the cover module 130.

A surface treatment layer may be further formed on a surface of the cover module 130 according to the embodiment of the present disclosure. The surface treatment layer is formed on the surface of the cover module 130 by anodizing so that the cover module 130 can be prevented from causing a short circuit with the gas sensing element, the NTC (negative temperature coefficient) thermistor, the resistance element or a terminal. The cover module 130 may be made of a metal material, and, examples of the metal material may include Al, Cu or SUS (Steel Use Stainless).

Figure 6:
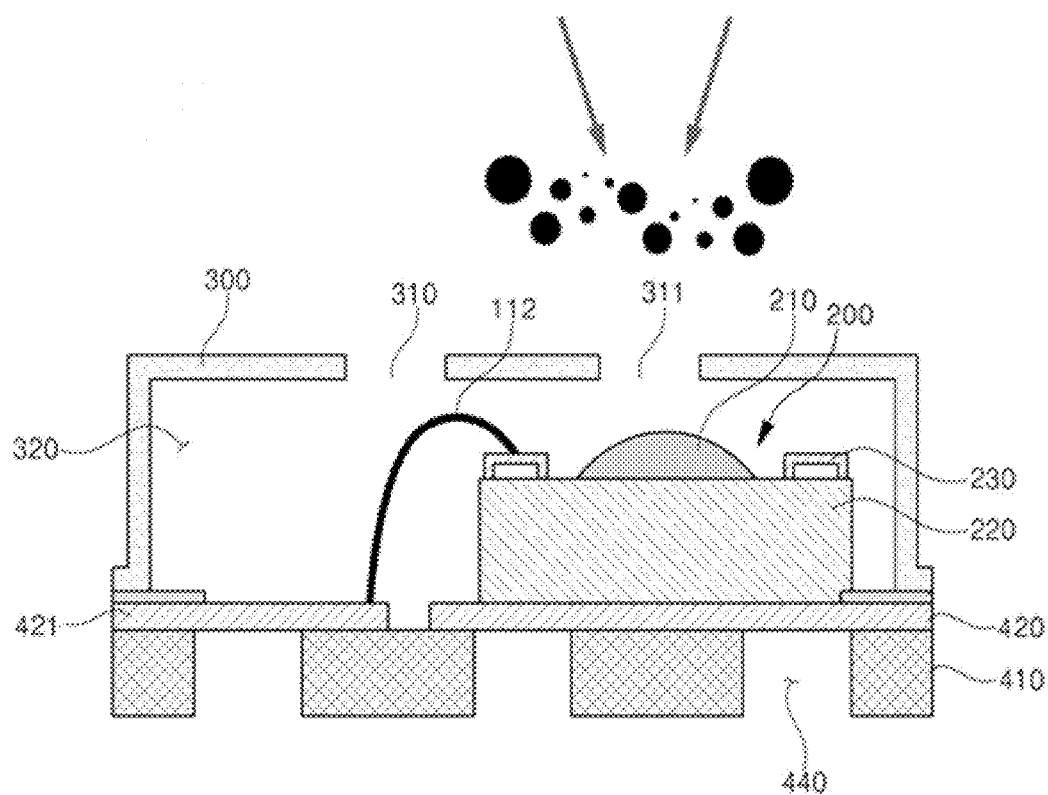
FIGS. 6 to 9 are views for explaining a gas sensor package according to another embodiment of the present disclosure.

FIG. 6 is a view of explaining a gas sensor package according to another embodiment of the present disclosure. A substrate 410 includes a plurality of metal patterns 420, and a gas sensing element 200 is mounted to the substrate 410. A cover module 300 configured for surrounding, sealing and receiving the substrate 410 and the gas sensing element 200 and includes ventilation holes 310, 311 which communicate with a receiving space 320 of the inside.

The substrate 410 is made of an insulating material and includes the plurality of metal patterns 420 whose surfaces are patterned with a metal material. The gas sensing element 200 is mounted to the metal patterns 420, and is bonded to a peripheral electrode 421 via a wire.

A bonding structure using the wire 112 shows an example of an electrical connection with the gas sensing element 200. In addition to the bonding using the wire 112, it is apparent that various connection methods, such as a flip chip bonding method and the like, may be adopted.

In the structure of FIG. 6, it is provided with the cover module 300 which is disposed to seal, receive and cover an entire upper part of the substrate 410 and the gas sensing element 200. The cover module 300 is configured such that an edge of the substrate 410 is adhered to an end of the cover module 300, and ventilation holes 310, 311 for the flow of gas are provided at an upper part.

The general gas sensor package is problematic that it is difficult to miniaturize the structure of a cap member in a mesh form used in the gas sensor package as described above. According to the embodiment of the present disclosure, the ventilation holes 310, 311 are formed at the upper surface of the integrally formed cover module so as to facilitate ventilation, and the receiving space is secured in the inside so that a sufficient gas contact space can be provided, thereby enhancing gas sensing efficiency.

The ventilation holes 310, 311 are configured to include the first movement hole 310 disposed at a position corresponding to the gas sensing portion, and the second movement hole 311 separated from the first movement hole 310 and configured to communicate with the inner part of the cover module. The second movement hole 311 is disposed at a position corresponding to the gas sensing portion 210 of the gas sensing element 200 so as to enhance a contact rate with gas entered into the position.

The cover module 300 includes side wall portions and an upper surface portion for covering an upper part of the side wall portions, and a lower part thereof is implemented in an open structure form. An end of each of the side wall portions has a bending portion which is bent outwardly. The bending portion of an end of the cover module 300 and a surface of the substrate 410 are adhered to each other so that the side wall portions of the cover module 300 can be bonded to the surface of the end of the substrate 410, thereby increasing sealing efficiency. A width of the substrate 410 and a width of the cover module 300 may be formed identical to each other.

In general, a size of the cap member in a mesh form of the general gas sensor package is smaller than that of the substrate, but according to the embodiment of the present disclosure, since the width of the substrate 410 and the width of the cover module 300 may be formed identical to each other, integrity of the package structure can be increased and bonding strength can be increased by the aforesaid boding structure. It is advantageous in that the damage of separation upon mounting the package to a device can be reduced.

A horizontal width of the cover module 300 and a horizontal width of the substrate 410 are formed in the same structure, connection portions may be formed not to have a stepped cone. This structure may enhance the integrity of a package structure and bonding strength.

Figure 7:
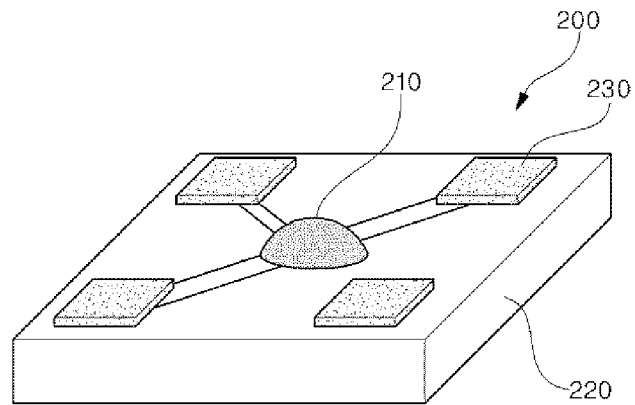
Figure 8:
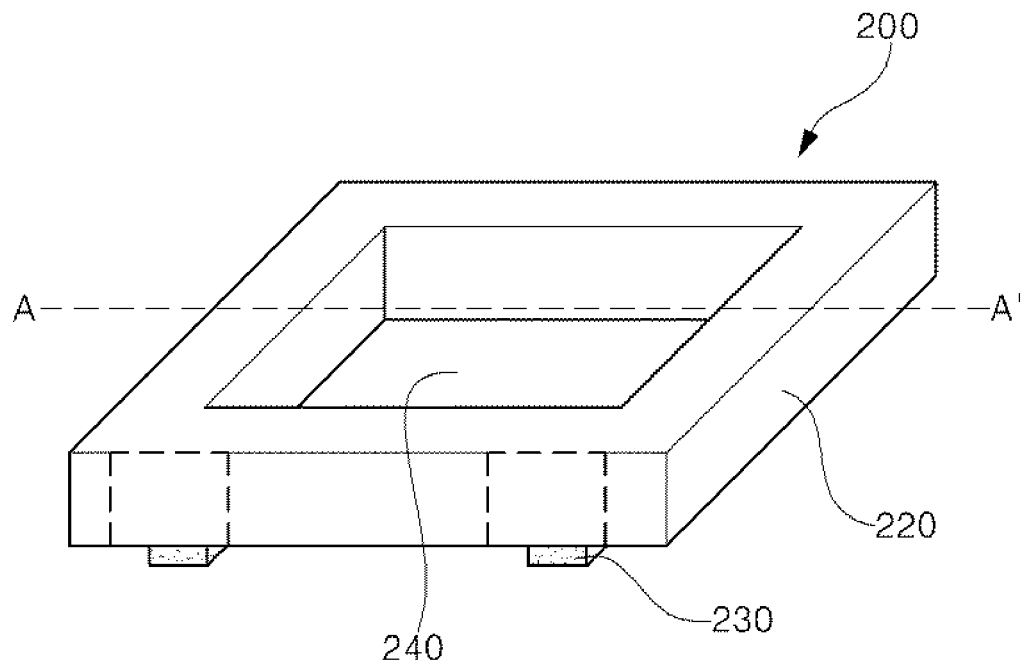
Figure 9:
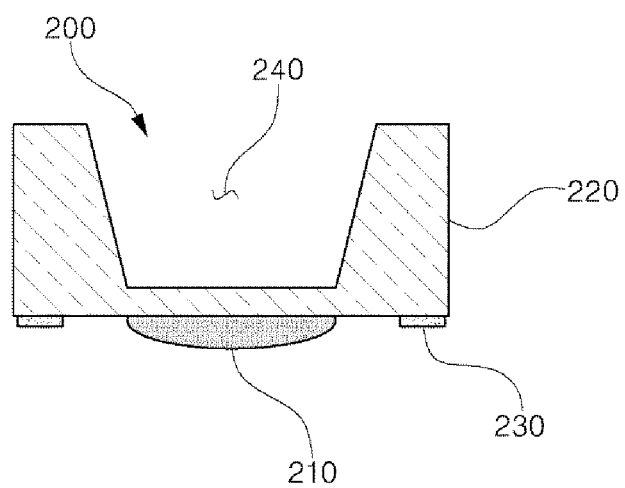

FIG. 7 is a top view of the gas sensing element according to the embodiment of the present disclosure. FIG. 8 is a bottom view of the gas sensing element according to the embodiment of the present disclosure. FIG. 9 is a cross-sectional view of the gas sensing element according to the embodiment of the present disclosure. FIG. 9 illustrates a section taken by lines A-A' of FIG. 8.

Referring to FIG. 7, the gas sensing portion 210 for detecting gas using a sensing material or a sensing chip is disposed on a surface of a body portion 220. An electrode pattern 230, which is connectable to an external terminal, is provided on an adjacent surface, so the gas sensing portion 210 and the electrode pattern 230 may be electrically connected to each other. As illustrated in FIGS. 8 and 9, a cavity portion 240 is formed in the body portion 220 so that the residence time of gas can be secured, and the gas sensing portion 210 may detect the gas entered into the gas sensor package.

Figure 12:
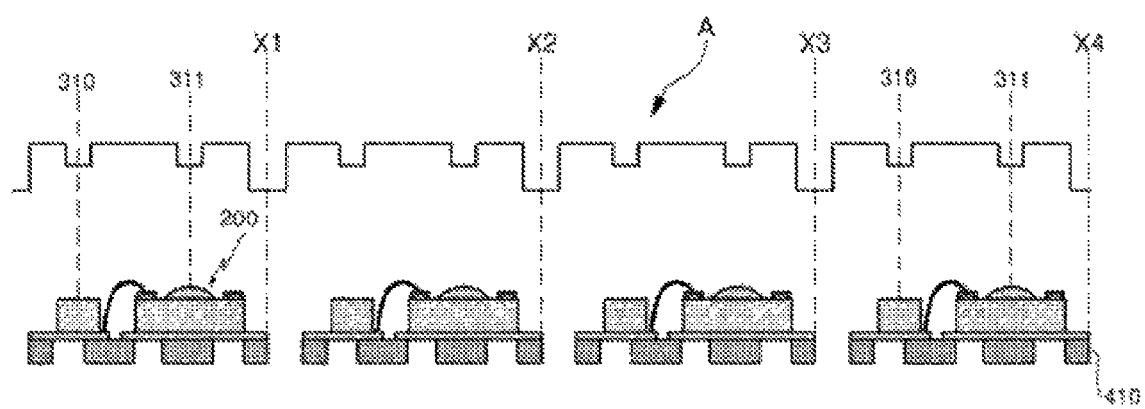

FIG. 10 is a view illustrating a cover module according to another embodiment of the present disclosure. FIGS. 11 and 12 are views for explaining a method of manufacturing the gas sensor package according to the embodiment of the present disclosure.

The cover module according to the embodiment of the present disclosure may be pre-formed in a structure in which the multiple cover modules having receiving spaces therein are provided by forming a mold through molding of a disk sheet structure A made of a polymer-based material, for example, PC (polycabonate), PE, PEEK and the like, and thus a receiving spaces. The disk sheet structure A may be formed in a plurality of structures in which two ventilation holes 310, 311 are formed on the unit cover module 300.

As shown in FIG. 11, the disk sheet structure A, which has been prepared in advance, is bonded to the substrate at a time by entirely aligning the disk sheet structure A in an upper part of the structure in which the multiple gas sensing elements are mounted to the substrate. The ventilation hole 310 and the gas sensing element 200 are bonded to the substrate 410 at a time in a state of being aligned. By cutting the structure based on cut surfaces X1, X2, X3, X4 after a curing process and the like, the gas sensor package in a single form may be manufactured.

The general gas sensor package is problematic in that time consumed for production is increased because molding is implemented using an epoxy-based material after the gas sensor chip has been mounted, and thus structures of DAM and the like are implemented through individual molding, and a process for mounting the cap member in the mesh form is then performed. On the contrary, the manufacturing process according to the embodiment of the present disclosure is advantageous in that the gas sensor package can be rapidly and produced in large quantities at a minimum process and cost because packaging is implemented by one bonding process, and the gas sensor package in unit is implemented by performing a cutting process.

As set forth above, according to some embodiments of the present disclosure, it can be provided with a gas sensor package capable securing a space, which enables gas to be in contact with the gas sensing portion, is secured by the cover module for covering and sealing the gas sensor, and having high sealing efficiency.

Also, according to some embodiments of the present disclosure, the first ventilation hole can enable gas to sufficiently flow into the gas sensing element in the cover module, and the second ventilation holes can discharge the reaction gas in the cover module so as to facilitate efficient ventilation, thereby enabling the problems of ventilation and radiant heat to be simultaneously settled.

An aspect of the present disclosure provides a gas sensor package that can secure a space which enables gas to be in contact with a gas sensing part through a cover module intended for covering and sealing a gas sensor, and can have high sealing efficiency.

Also, another aspect of the present disclosure provides a gas sensor package which can simultaneously solve the problems of ventilation and radiant heat by enabling a reaction gas to sufficient flow into a gas sensing element in a cover module via a first ventilation hole and discharging the reaction gas in the cover module via second ventilation holes to facilitate effective ventilation.

According to an aspect of an embodiment of the present disclosure, there is provided a gas sensor package including: a substrate; a gas sensing element on the substrate; and a cover module including ventilation holes and configured for covering the gas sensing element.

According to another embodiment of the present disclosure, the ventilation holes may be formed to communicate with a receiving space of an inner portion of the cover module.

According to still another embodiment of the present disclosure, the ventilation holes may include: a first ventilation hole formed at side wall portions of the cover module; and second ventilation holes formed in an upper surface portion of the cover module.

According to still another embodiment of the present disclosure, the upper surface portion of the cover module is formed parallel to a plane of the substrate, and the side wall portions of the cover module may be formed perpendicular to the plane of the substrate.

According to still another embodiment of the present disclosure, the first ventilation hole or the second ventilation holes may be aligned to correspond to a center part of the gas sensing element.

According to still another embodiment of the present disclosure, the first ventilation hole may be configured such that at least one first ventilation hole is formed at each of the side wall portions.

According to still another embodiment of the present disclosure, the first ventilation hole may be formed to contact the substrate.

According to still another embodiment of the present disclosure, the first ventilation hole may be formed to be symmetric based on the gas sensing element.

According to still another embodiment of the present disclosure, the second ventilation holes may be configured such that the multiple send ventilation holes are formed in the upper surface portion of the cover module.

According to still another embodiment of the present disclosure, the cover module may be bonded to an end of the substrate.

According to still another embodiment of the present disclosure, the side wall portions of the cover module may be bonded to a surface of the end of the substrate.

According to still another embodiment of the present disclosure, the cover module may be made of a metal material and may further include a surface treatment layer.

According to still another embodiment of the present disclosure, the gas sensor package may further include an output change portion formed on the substrate and configured for changing an output mode of the gas sensing element.

According to still another embodiment of the present disclosure, the output change portion may be composed of an NTC (negative temperature coefficient) thermistor or a resistance element.

According to still another embodiment of the present disclosure, the gas sensor package may further include an adhesive material layer for bonding the cover module to the substrate.

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A gas sensor package, comprising:
a substrate;
a metal pattern disposed on a top surface of the substrate;
a gas sensing element on the substrate; and
a cover module including ventilation holes, and the cover module for covering the gas sensing element,
wherein the gas sensing element includes:
   a body portion;
   an electrode pattern disposed under the body portion; and
   a gas sensing part having a gas sensing material, wherein the gas sensing part and the electrode pattern are disposed between the body portion and the metal pattern,
wherein the ventilation holes include:
   a first ventilation hole formed at side wall portions of the cover module, and
   a second ventilation hole formed on an upper surface portion of the cover module,
   wherein the first ventilation hole is aligned to correspond to a center part of a side surface of the gas sensing part,
   wherein the second ventilation hole is aligned to correspond to a center part of an upper surface of the gas sensing element,
   wherein the first ventilation hole enables a reaction gas to flow into the cover module,
   wherein the second ventilation hole discharges the reaction gas entered into the cover module, and
   wherein the gas sensing part is face to face with the top surface of the substrate and is exposed through the first ventilation hole.

2. The gas sensor package of claim 1, wherein the first and second ventilation holes communicate with a receiving space of an inner portion of the cover module.

3. The gas sensor package of claim 1, wherein the upper surface portion of the cover module is parallel to a plane of the substrate, and the side wall portions of the cover module are perpendicular to the plane of the substrate.

4. The gas sensor package of claim 1, wherein the first ventilation hole is configured such that at least one first ventilation hole is formed at each of the side wall portions of the cover module.

5. The gas sensor package of claim 1, wherein the first ventilation hole is formed to contact the substrate.

6. The gas sensor package of claim 1, wherein the second ventilation holes are in plural number at the upper surface portion of the cover module.

7. The gas sensor package of claim 1, wherein the cover module is bonded to an end of the substrate.

8. The gas sensor package of claim 1, wherein the side wall portions of the cover module are bonded to a surface of an end of the substrate.

9. The gas sensor package of claim 1, wherein the cover module is made of a metal material and includes a surface treatment layer.

10. The gas sensor package of claim 1, further comprising an output change portion formed on the substrate to change an output mode of the gas sensing element.

11. The gas sensor package of claim 10, wherein the output change portion is a NTC (negative temperature coefficient) thermistor or a resistance element.

12. The gas sensor package of claim 1, further comprising an adhesive material layer for bonding the cover module to the substrate.

13. The gas sensor package of claim 1, wherein the gas sensing element is in direct physical contact with the metal pattern.

* * * * *